United States Patent [19]
Fauconet et al.

[11] Patent Number: 5,734,075
[45] Date of Patent: Mar. 31, 1998

[54] PROCESS FOR RECOVERY OF THE LIGHT NOBLE PRODUCTS PRESENT IN THE DISTILLATION RESIDUES FROM THE PROCESSES FOR THE MANUFACTURE OF ACRYLIC ACID AND OF ITS ESTERS

[75] Inventors: Michel Fauconet, Valmont; Norbert Richard, Saint Avold; Patrick Delafin, Saint Auban, all of France

[73] Assignee: Elf Atochem S.A., Puteaux, France

[21] Appl. No.: 570,773

[22] Filed: Dec. 12, 1995

[30] Foreign Application Priority Data

Dec. 12, 1994 [FR] France ................... 94 14935

[51] Int. Cl.$^6$ ................... C07C 67/48; C07C 51/42
[52] U.S. Cl. ................... 560/218; 560/216; 560/205; 562/598; 562/600
[58] Field of Search ................... 560/218, 216, 560/205; 562/598, 600

[56] References Cited

U.S. PATENT DOCUMENTS

| | | | |
|---|---|---|---|
| 3,086,046 | 4/1963 | Kutepow et al. | 260/526 |
| 3,868,410 | 2/1975 | Horlenko . | |
| 4,317,926 | 3/1982 | Sato . | |

FOREIGN PATENT DOCUMENTS

| | | |
|---|---|---|
| 1307204 | 12/1961 | France . |
| 2194681 | 3/1974 | France . |
| 2261252 | 9/1975 | France . |
| 2415092 | 8/1979 | France . |

OTHER PUBLICATIONS

Abstract, No. 93–0080347/10, JP 5–025086 (Dec. 7, 1991).
Abstract, No. 75–66337W/40, JP 75–69014 (Sep. 6, 1975).
Abstract, No. 68–13277Q/00, FR 1,572,316, (Jun. 27, 1969).
Abstract, No. 116:60173g, JP 3–178949 (Aug. 2, 1991).
Abstract, US 2,806,678 (Sep. 17, 1957).
Abstract, No. 94–115152/14, JP 6–655149 (Dec. 8, 1992).
Abstract, No. 97:128273m, JP 57–062229 (Apr. 15, 1982).
Abstract, No. 95900 D/52, JP 56–147745 (Apr. 21, 1980).

*Primary Examiner*—José G. Dees
*Assistant Examiner*—Jean F. Vollano
*Attorney, Agent, or Firm*—Millen, White, Zelano, & Branigan, P.C.

[57] ABSTRACT

Figure 1:
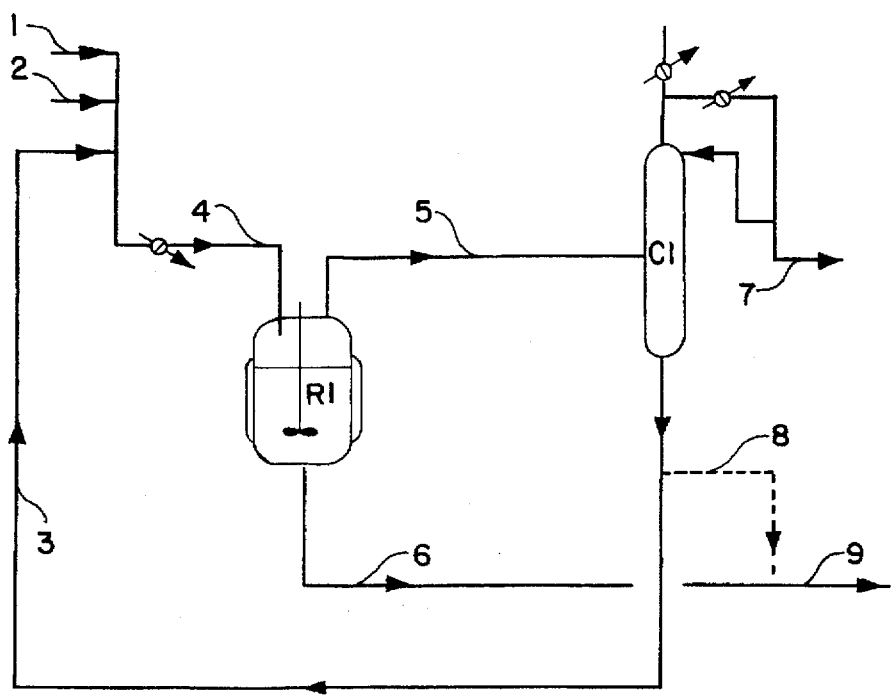

To recover these noble products consisting of acrylic acid monomer, acrylic ester monomers and alcohols, a thermal cracking is performed in the absence of catalyst on a mixture of heavy distillation residues originating, on the one hand, from the manufacture of acrylic acid and, on the other hand, from the manufacture of the esters, the light fraction originating from the dissociation reactions is continuously vaporized during the cracking operation and this light fraction is distilled in order to recover, after condensation, the required products. The process according to the invention may consist in conducting the cracking of the mixture of heavy residues, optionally preheated, in a reactor (R1); feeding a distillation column (C1) with the light cracking products; recovering the required mixture of light noble products at the head of column (C1); recycling the flow recovered at the foot of column (C1) into the reactor (R1); recovering the heavy residue from the reactor (R1) and sending it to a removal treatment, if appropriate after having diluted it with a part of the flow recovered at the foot of column (C1), the remainder of the said flow being recycled into the reactor (R1). Figure to be published: FIG. 1

9 Claims, 1 Drawing Sheet

PROCESS FOR RECOVERY OF THE LIGHT NOBLE PRODUCTS PRESENT IN THE DISTILLATION RESIDUES FROM THE PROCESSES FOR THE MANUFACTURE OF ACRYLIC ACID AND OF ITS ESTERS

The present invention relates to a process for recovery of the light noble products present in the distillation residues from the processes for the manufacture of acrylic acid and of the esters of the said acid and of $C_1$–$C_8$ alcohols, by thermal dissociation (or cracking) of the said residues. Noble products are intended to mean acrylic acid monomer, the said acrylic ester monomers and the said alcohols.

In processes for the synthesis of acrylic acid employing, for example, catalytic oxidation of propylene, heavy byproducts are obtained, which are removed at the foot of the final distillation columns. These mixtures of heavy compounds contain chiefly the derivatives

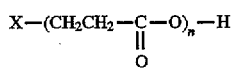

n being higher than or equal to 1,
which are generated by reactions of condensation, with the double bond of acrylic acid:
of acrylic acid itself

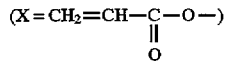

of acetic acid

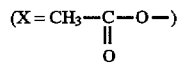

of water (X=HO—)

Similarly, in processes for the synthesis of the esters from acrylic acid, the heavy products removed at the foot of the distillation columns contain the corresponding esters of these compounds with the alcohol employed during the syntheses of these esters, as well as the products of condensation of the alcohols (X=RO—, R=$C_1$–$C_8$ alkyl) with the double bonds of the above compounds.

In addition, a proportion of the polymerization inhibitors employed in the processes is encountered again in these mixtures of heavy products.

These mixtures of heavy products can be evaporated in order to recover the main part of the monomers (acrylic acid and esters) which they contain. In the absence of a suitable process for reclaiming them, the residues obtained are then lost, and this represents a large quantity of waste which is difficult to remove, and also a loss of monomers and alcohols.

Recovery of monomers by liquid-phase thermal dissociation of the derivatives of addition to the acrylic double bond is well described in the literature.

The main problem with a thermal dissociation treatment of this type, when applied to an actual mixture of heavy products obtained at the foot of the final acrylic acid distillation columns, is the high viscosity of the residue, which becomes incapable of being conveyed in conduits. This excessive viscosity is accompanied by an insoluble tar deposit which causes fouling of the wall of the cracking reactor, entailing a decrease in the efficiency of heat transfer through the wall, and, as a final consequence, a reduction in the cracking yield. These fouling phenomena make frequent cleaning operations necessary at regular intervals, and these make this manner of operating incompatible with a continuous regime and reduce the output efficiency in a noncontinuous regime.

The viscosity of the residue obtained as a result of the cracking increases with the residence time at high temperature of the mixture of heavy products to be treated and with the quantity of light monomers recovered by distillation. To obtain a viscosity of the residue which is compatible with the normal transfer conditions for liquid flows, and to reduce the fouling phenomena, these two parameters must necessarily be limited, and this has the effect of reducing the cracking yield.

These disadvantages are reduced when the treatment is applied to the recovery of noble products in the heavy ends resulting from the manufacture of acrylic esters, as described in French Patent FR-B-2 194 681.

The processes which are described for the recovery of noble products in the heavy products of manufacture of acrylic acid are essentially catalytic. The catalysts described are very varied: carboxylates, phosphates, borates (FR-A-2 261 252), acids such as $H_2SO_4$ (JP-05 025086), alumina or silica (JP-75 69014), secondary or tertiary amines or phosphines (FR-1 572 316), solid acids such as zeolites (JP-03 178 949), catalysts of Friedel and Crafts type (U.S. Pat. No. 2,806,878) and alkoxide titanates (JP-06 0655149).

Besides the fact that these processes do not solve the key problem of the limitation of the recovery yield because of the excessive viscosity of the residues and of the formation of undesirable tars, other disadvantages are related more particularly to the use of catalysts:
 cost of the catalyst;
 corrosion phenomena;
 difficulty of removal in the heavy residues, resulting in a high cost of waste treatment:
  inorganic waste which is difficult to incinerate;
  presence of metallic residues causing fouling of the incineration furnaces;
  removal by aqueous washes, causing an increase in the pollution discharged in aqueous waste;
 problems of deactivation of the solid catalysts, due to the fouling of the active catalytic pores by deposits of partially polymerized compounds.

To reduce these disadvantages, U.S. Pat. No. 3,086,046 describes a noncatalytic treatment consisting of an evaporation of the mixture to be cracked, followed by a vapour-phase thermal dissociation, at very high temperature (350°–650° C.) at a pressure of $6.7 \times 10^2$–$2 \times 10^4$ Pa (5–150 mm Hg). This process, suitable for the treatment of mixtures which are very rich in products of low molecular mass (acrylic acid and acrylic acid dimer) cannot be employed in the case of an actual heavy distillation residue obtained, for example, within the context of the process for the manufacture of acrylic acid from propylene and oxygen. The fraction of the mixture which is vaporized in the first stage would be reduced in this case by the small quantity of products of sufficiently low boiling points, or the increase in this fraction would require a vaporization temperature such that the problem of the high viscosity of the residues removed at the bottom of the vaporizer would again become a limitation.

Water extraction of the acrylic acid present in the reaction mixture from thermal dissociation is claimed in several patents: FR-A-2 415 092, JP-57 062 229, which employs a basic aqueous solution, and JP-56 147 745, which describes a process using addition of water followed by extraction with an organic solvent. The major disadvantage of these processes is that the regenerated monomer(s) is (are) not removed from the mixture as it is (they are) formed during the thermal dissociation reaction. As a result, an instantaneous recombination (reverse reaction) of the addition or polymerization derivatives, starting from the dissociated products present in this mixture, cannot be avoided.

Another way of reducing the problem of the excess viscosity of the heavy residues obtained by thermal cracking of the heavy ends from the manufacture of acrylic acid would be to employ a solvent. The disadvantage of such a process is that it would demand a costly recovery of the solvent employed.

Surprisingly, it has been discovered that the fact of operating the thermal dissociation or cracking of the heavy products of the synthesis of acrylic acid in the presence of heavy products recovered at the foot of the final columns for the manufacture of acrylic esters, with instantaneous distillation of the light products which are generated, makes it possible to improve the recovery yield appreciably, while reducing the fouling in the dissociation reactor and the viscosity of the residue obtained at the outcome of the thermal dissociation operation.

The subject of the present invention is therefore a process as defined in the introduction of this description, this process being characterized in that this cracking is carried out in the absence of catalyst, on a mixture of heavy distillation residues originating, on the one hand, from the manufacture of acrylic acid and, on the other hand, from the manufacture of the abovementioned esters of the said acid, in that the light fraction originating from the dissociation reactions is vaporized continuously during the cracking operation and in that this light fraction is distilled in order to recover, after condensation, the required light noble products.

In the mixture of the residues subjected to the process of the invention the mass ratio of the heavy residues originating from the process for the manufacture of acrylic acid to the heavy residues originating from the process for the manufacture of an ester of acrylic acid is advantageously between 9/1 and 1/9.

The cracking is advantageously conducted at a temperature of between 140° and 260° C., preferably between 180° and 220° C., with a residence time of 0.5 to 3 hours.

The distillation of the vaporized light fraction is advantageously conducted at reduced pressure, and also advantageously in the presence of at least one polymerization inhibitor, it being possible for the polymerization inhibitor (s) to be introduced via the introduction of a part of the flow feeding the distillation column.

In accordance with an advantageous characteristic of the process according to the invention, the light noble products obtained are recycled to the ester manufacture unit from which the heavy residues employed originate together with the heavy residues originating from the manufacture of acrylic acid.

In accordance with a first embodiment of the process according to the invention, conducted continuously, the operations are performed, consisting in:

conducting the cracking of the mixture of the heavy residues to be cracked, optionally preheated, in a reactor (R1);

feeding a distillation column (C1) with the light products of the cracking;

recovering, at the head of column (C1), the required mixture of light noble products;

recycling into the reactor (R1) the flow recovered at the foot of the column (C1);

recovering the heavy residue from the reactor (R1) and sending it to a removal treatment, if appropriate after having diluted it with a part of the flow recovered at the foot of the column (C1), the remainder of the said flow being recycled into the reactor (R1).

In accordance with a second embodiment of the present invention, the mixture of heavy products used is distilled simultaneously with the light ends recovered at the end of the cracking stage and the cracking reactor is fed with the mixture of heavy ends obtained at the foot of a distillation column. This method of operation is particularly suited to the treatment of heavy ends which are rich in uncombined light products (acrylic acid, ester monomers and alcohols). Conducted continuously, it includes the operations consisting in:

sending the mixture of the heavy residues to be cracked to a distillation column (C'1);

recovering, at the head of column (C'1), a mixture of light noble products;

sending the flow obtained at the foot of column (C'1) to a cracking reactor (R'1);

recycling the mixture of the light products of cracking to the distillation column (C'1);

recovering the heavy residue from the reactor (R'1) and sending it to a subsequent removal treatment, if appropriate after having diluted it with a part of the flow recovered at the foot of the column (C'1), the remainder of the said flow being sent to the cracking reactor (R'1).

In order better to illustrate the process of the present invention, the abovementioned two embodiments will be described in greater detail below with reference to the FIGS. 1 and 2 respectively, each of which shows the corresponding plant diagram.

If reference is made first of all to FIG. 1, it can be seen that a mixture of heavy products originating from the manufacture of acrylic acid (conduit 1), of heavy products originating from the manufacture of acrylic ester (conduit 2) and of a part of the flow recovered at the bottom of column C1 (conduit 3) is delivered to the cracking reactor R1 via the conduit 4. Thus constituted, this mixture is optionally preheated before being delivered to the cracking reactor R1. The latter is heated and the mixture of light products which are obtained is delivered, via conduit 5, as feed to the column C1, which preferably operates at a reduced pressure. Into the upper part of column C1 is delivered a polymerization inhibitor chosen from the conventional inhibitors or a mixture of these inhibitors (phenothiazine, hydroquinone, phenols, phenol ethers and the like). The stabilization of the upper part of the column may (advantageously) be ensured by virtue of the introduction at the head of a part of the flow feeding the column. A mixture of light products, part of which forms the reflux, is recovered, after condensation at the head of the column C1. The distilled product, practically free from heavy products, consists essentially of acrylic acid, of acrylic ester monomer, of alcohol and of water. This mixture of light noble products may be advantageously recycled (conduit 7) upstream of the process for the manufacture of the acrylic ester which has provided the heavy ends conveyed into R1 via the conduit 2.

The residue obtained at the bottom of reactor R1 (conduit 6) may be optionally diluted with a part of the flow recovered at the foot of column C1 (conduit 8). The remainder of the flow obtained at the foot of column C1 is conveyed as feed to the reactor R1 (conduit 3). The spent heavy residue is conveyed to a subsequent conventional removal treatment (conduit 9).

Figure 2:
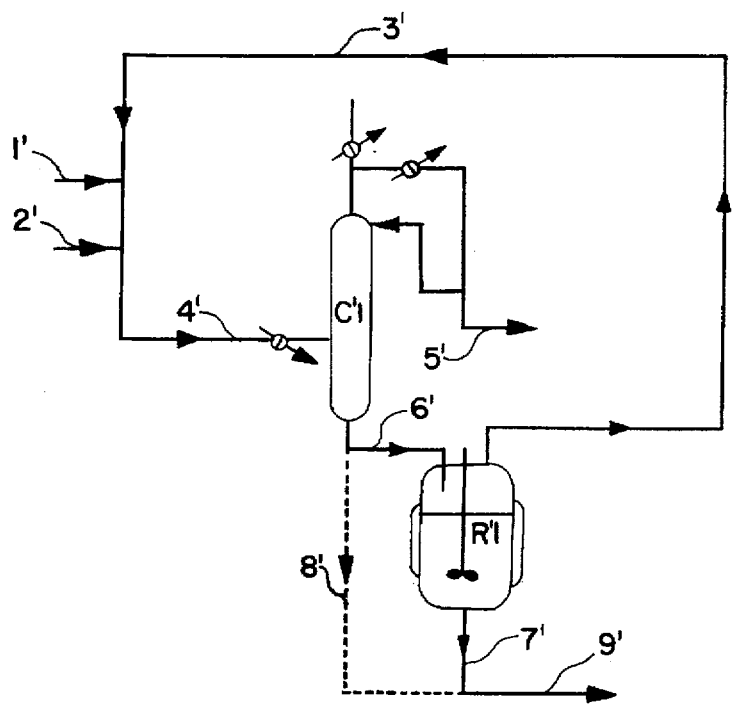

If reference is now made to FIG. 2, it can be seen that the mixture of heavy products originating from the manufacture of acrylic acid (conduit 1'), of heavy products originating from the manufacture of acrylic ester (conduit 2') and all or part of the light ends flow recovered at the head of the cracking reactor R'1 (conduit 3') is delivered as feed to the column C'1 (conduit 4').

Column C'1 operates preferably at a reduced pressure and a polymerization inhibitor is delivered to its upper part, as indicated in the case of the first embodiment. It allows most of the heavy products to be separated off at the foot of the column. The distilled product consists essentially of acrylic acid, of acrylic ester monomer, of alcohol and of water. This mixture of light noble products may be advantageously recycled (conduit 5') upstream of the process for the manufacture of the acrylic ester which has provided the heavy ends delivered to C'1 via the conduit 2'.

The flow obtained at the foot of column C'1 is delivered to the cracking reactor R'1 (conduit 6'). The reactor R'1 is heated and the vaporized mixture of light products is delivered as feed to the column C'1, via the conduit 3'. The flow of spent heavy residue originating from the cracking reactor R'1, via the conduit 7', may be optionally diluted with a part of the flow collected at the foot of the column C'1 (conduit 8'). This spent heavy residue is delivered to a subsequent conventional removal treatment (conduit 9').

The present invention is illustrated further by the following examples. In these examples the percentages are expressed by weight and the following abbreviations have been employed:

AA: acrylic acid
AAH: fraction of heavy products originating from the manufacture of AA
EA: ethyl acrylate
EAH: fraction of heavy products originating from the manufacture of EA
MA: methyl acrylate
MAH: fraction of heavy products originating from the manufacture of MA
AA dimer and trimer: compounds of formulae, respectively,

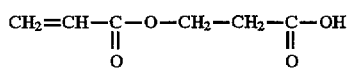

and

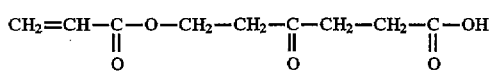

originating from the condensation of acrylic acid with itself

EAP: ethyl acryloyloxypropionate (ethyl ester of the AA dimer)
MAP: methyl acryloyloxypropionate (methyl ester of the AA dimer)
EEP: ethyl 2-ethoxypropionate (derived from addition of ethanol to the double bond of EA)
MMP: methyl 2-methoxypropionate (derived from addition of methanol to the double bond of MA).
Cracking ratio: ratio, expressed as mass percentage, of the light fraction recovered during the cracking to the mixture of heavy ends introduced into the reactor.
Recovery ratio of AA and of the esters: ratio, expressed as mass percentage, of the AA and ester monomers recovered in the fraction distilled during the cracking operation, to the mixture of heavy ends introduced into the reactor.

EXAMPLE 1

200 g of mixtures of AAH and EAH are introduced into a stirred reactor, 0.5 liters in capacity, heated with an oil bath, supporting a short column provided with a few Vigreux points acting as a demister and supporting a condenser and a receiver. The mixtures are heated to boiling and the light products generated by the reaction are distilled.

The AAH mixture is made up of 2.8% of AA, 25.4% of AA dimer and 9.8% of hydroquinone, the remainder being made up essentially of heavier condensation products of AA.

The EAH mixture consists of 9.2% of AA monomer, 8.8% of AA dimer, 0.08% of EA, 0.08% of ethanol and 1.3% of hydroquinone, the remainder being chiefly made up of EAP, EEP and heavier condensation products of AA or of EA.

Tables 1 to 4 below summarize the results of a number of tests carried out with various AAH/EAH ratios, for different cracking ratios. The temperatures reached during the tests are between 190° C. and 250° C.

The results are expressed as:

the viscosity of the residue obtained at the end of the cracking experiment. This viscosity is expressed in centipoises (Pa s) and is measured at a temperature of 100° C. (Table 1). The very clear decrease in the viscosity of the residue obtained after cracking, when a mixture of AAH and EAH is employed, is noted, when compared with a cracking carried out by starting from the AAH fraction alone;

the recovery ratio of AA and of EA (Tables 2 and 3).

By extrapolating these results it is possible to calculate the recovery ratios of AA and of EA for an equivalent viscosity of the residue after cracking. Table 4 gives the results of this calculation for a residue viscosity of 500 Pa s at 100° C.

TABLE 1

Viscosity, in Pa s at 100° C., of the heavy residue after cracking

| AAH/EAH Cracking ratio | 100/0 | 60/40 | 50/50 | 40/60 | 0/100 |
|---|---|---|---|---|---|
| 30% | 280 | 30 | 20 | 13 | 4 |
| 40% | 1100 | | | | |
| 50% | >10 000 | 174 | 85 | 46 | 7 |
| 60% | | 3440 | 381 | | |
| 70% | | | | 180 | 21 |

TABLE 2

Recovery ratio of AA in g/100 g of heavy ends introduced

| AAH/EAH Cracking ratio | 100/0 | 60/40 | 50/50 | 40/60 | 0/100 |
|---|---|---|---|---|---|
| Initial AA (%) | 2.8 | 5.4 | 6 | 6.6 | 9.2 |
| 30% | 30.2 | 22.3 | 20.9 | 19.1 | 14 |
| 40% | 39.2 | | | | |
| 50% | 48.7 | 35 | 32.7 | 31.1 | 18.4 |
| 60% | | 40.7 | 37.1 | | |
| 70% | | | | 36.9 | 23.1 |

TABLE 3

Recovery ratio of EA in g/100 g of heavy ends introduced

| AAH/EAH Cracking ratio | 100/0 | 60/40 | 50/50 | 40/60 | 0/100 |
|---|---|---|---|---|---|
| Initial EA (%) | 0 | 0.1 | 0.1 | 0.1 | 0.1 |
| 30% | | 1.4 | 1.8 | 1.9 | 2.4 |
| 40% | | | | | |
| 50% | | 2.9 | 3.4 | 4.2 | 3.8 |
| 60% | | 4.8 | 4.6 | | |
| 70% | | | | 7.9 | 6 |

TABLE 4

Recovery ratio extrapolated for a residue viscosity of 500 Pa s at 100° C.

| | Cracking ratio | Recovery ratio (%) | | |
|---|---|---|---|---|
| AAH/EAH | 500 Pa s (%) | AA | EA | Sum |
| 100/0 | 35 | 35 | 0 | 35 |
| 60/40 | 56 | 38 | 3.8 | 41.8 |
| 50/50 | 62 | 37.5 | 4.8 | 42.3 |
| 40/60 | 66 | 36 | 7 | 43 |
| 0/100 | 85 | 26 | 8.3 | 34.3 |

Table 4 shows the improvement in the recovery ratio of monomers by cracking mixtures of AAH and EAH, compared with that obtained with either the AAH fraction or the EAH fraction.

EXAMPLE 2

The operation is carried out continuously according to the process shown diagrammatically in FIG. 1, in an assembly constructed as described below:

(a) Reaction section:
   a preparation receiver into which the mixture of heavy products to be cracked is charged, 1 liter in capacity, equipped with a mechanical stirrer, a jacket heated with oil at a temperature controlled at 90° C.; this preparation receiver feeds the cracking reactor continuously;

a cracking reactor R1 0.5 liter in capacity, equipped with a mechanical stirrer, a jacket in which oil circulates at a controlled temperature, a lagged outlet at the bottom of the reactor for removing the residue of the cracking reaction, and a temperature probe. Above this reactor there is a short lagged column provided with Vigreux points for avoiding the entrainment of liquid phase (demister) and a condenser, after the demister, fed with water at 20° C.;

a lagged receiver which receives the heavy residue obtained at the foot of the cracking reactor R1;

a receiver which receives the mixture of light ends condensed at the head of the reactor R1.

(b) Distillation section:
   an adiabatic Vigreux column C1 with an efficiency of 6 theoretical plates, fed continuously with the mixture of light products condensed at the head of reactor R1, equipped with:
      a reboiler with a thermal syphon at the foot, fed in its outer wall with oil at a controlled temperature;
      a head condenser, fed with water at 20° C.;
      a head temperature probe;
      a draw-off system allowing a proportion of the condensed liquid phase to be returned to ensure a reflux at the head of the column;
      a vacuum pump system equipped with a control, enabling a reduced pressure to be maintained in the column;
      an injection of phenothiazine in solution at a concentration of 1% in acrylic acid at the head of the column;
   a receiver which receives the flow leaving at the foot of column C1;
   a receiver which receives the mixture of light products distilled at the head of column C1.

The operating conditions and the results obtained in the reaction section are summarized in Table 5 for various mixtures of heavy products to be cracked:

AAH/EAH mixture=50/50 which has the following composition: AA monomer: 3.8%, AA dimer: 15.6%, EA: 0.06%, ethanol: 0.3%, the remainder being made up essentially of heavier condensation products of AA or of EA.

AAH/MAH mixture=50/50 which has the following composition: AA monomer: 1.3%, AA dimer: 9.4%, MA: 0.01%, methanol: 0.09%, the remainder being made up essentially of heavier condensation products of AA or of MA.

AAH alone, which has the following composition: AA monomer: 1.8%, AA dimer: 22.5%, AA trimer: 4.1%, hydroquinone: 9.8%, the remainder being made up essentially of heavier condensation products of AA.

TABLE 5

Viscosity and recovery ratio for various mixtures of heavy ends - continuous reaction

| | | AAH/EAH = 50/50 | | AAH/MAH = 50/50 | | | AAH alone | |
|---|---|---|---|---|---|---|---|---|
| R1 temperature | °C. | 206 | 221 | 203 | 206 | 216 | 200 | 230 |
| R1 residence time | min | 54 | 54 | 55 | 59 | 53 | 75 | 74 |
| Cracking ratio | % | 41 | 61 | 37 | 46 | 56 | 34 | 49 |
| Viscosity at 100° C. | Pa s | 34 | 1055 | 69 | 277 | 1285 | 4210* | >10 000* |
| Recovery ratio: | | | | | | | | |
| - AA | % | 25.5 | 34.9 | 22.1 | 27.5 | 29.9 | 31.4 | 42.5 |
| - ester | % | 2.4 | 3.7 | 2.8 | 4.4 | 4.3 | 0 | 0 |
| - alcohol | % | 0.5 | 0.7 | 0.3 | 0.3 | 0.4 | 0 | 0 |

*: blockage of the conduit for removal of the residue

Here, again, a large reduction in the viscosity of the heavy residue obtained at the foot of reactor R1 is observed, together with an increase in the recovery ratio for an equivalent viscosity, after thermal cracking in the mixtures of AAH and EAH and of AAH and MAH, when compared with the treatments carried out based on the AAH fraction alone. In particular, the viscosities which are higher than 4000 Pa s (measured at 100° C.), obtained during the cracking of the AAH fraction alone are too high to permit a steady flow of the residue obtained.

After this thermal cracking stage the light ends recovered at the head of reactor R1 are distilled continuously on the set-up described above. The operating conditions and results obtained are summarized in Tables 6 and 7.

TABLE 6

Operating conditions and results from the distillation stage - AAH/EAH cracking

| Analyses of the C1 feed (%) | | Distillation operating conditions | | Analyses of the C1 distillate (%) | |
|---|---|---|---|---|---|
| AA | 64.3 | Flow rates (g/h): | | AA | 81.7 |
| AA dimer | 0.7 | feed | 250 | EA | 12 |
| EA | 9.7 | head draw-off | 180 | Ethanol | 1.9 |
| Ethanol | 1.7 | Pressure Pa (mm Hg) | 6.7 × 10³ (50) | EEP | 0.2 |
| EEP | 4.6 | Head temperature (°C.) | 57 | H₂O | 4.2 |
| EAP | 5.7 | | | | |
| H₂O | 5.6 | | | | |

TABLE 7

Operating conditions and results from the distillation stage - AAH/MAH cracking

| Analyses of the C1 feed (%) | | Distillation operating conditions | | Analyses of the C1 distillate (%) | |
|---|---|---|---|---|---|
| AA | 65.5 | Flow rates (g/h): | | AA | 87.6 |
| dimer | 1.4 | feed | 200 | MA | 6.2 |
| MA | 7.7 | head draw-off | 120 | Methanol | 0.9 |
| Methanol | 1.2 | Pressure Pa (mm Hg) | 6 × 10³ (45) | MMP | 0.7 |
| MMP | 1.5 | Head temperature (°C.) | 51 | H₂O | 4.5 |
| MAP | 10.9 | | | | |
| H₂O | 5 | | | | |

EXAMPLE 3

The operation is carried out continuously according to the process shown diagrammatically in FIG. 2, in a set-up constructed as described below:

(a) Distillation section:
   a preparation receiver, 1 liter in capacity, into which are charged the mixture of AAH and EAH to be cracked and the light ends obtained during the cracking reaction. This receiver is equipped with a mechanical stirrer, a jacket heated with oil at a temperature controlled at 90° C.;
   an adiabatic Vigreux column C'1 with an efficiency of 12 theoretical plates, fed continuously, in the middle of the column, with the mixture contained in the preparation receiver, and equipped with:
      a reboiler with a thermal syphon at the foot, fed in its outer wall with oil at a controlled temperature;
      a head condenser fed with water at 20° C.;
      a head temperature probe;
      a draw-off system enabling part of the condensed liquid phase to be returned to ensure a reflux at the head of the column;
      a vacuum pump system equipped with a control, enabling a reduced pressure to be maintained in the column;
      an injection of phenothiazine in solution at a concentration of 1% in AA at the head of the column;
   a receiver which receives the flow leaving at the foot of column C'1;
   a receiver which receives the mixture of light products distilled at the head of column C'1.

(b) Reaction section:
   a cracking reactor R'1 of 0.5 liter capacity, equipped with a mechanical stirrer, a jacket in which oil circulates at a controlled temperature, a lagged outlet at the bottom of the reactor for removing the residue of the cracking reaction and a temperature probe. Above this reactor is a short lagged column provided with Vigreux points to avoid the entrainment of liquid phase (demister) and a condenser, after the demister, fed with water at 20° C. It is fed continuously with the product obtained at the foot of column C'1;
   a lagged receiver which receives the residue obtained at the foot of the cracking reactor R'1;
   a receiver which receives the mixture of light ends condensed at the head of the reactor R'1.

The operating conditions and results obtained during the experimental simulation of the distillation stage are summarized in Table 8. Those from the cracking reaction stage are listed together in Table 9.

TABLE 8

Operating conditions and results of the distillation stage

| Operating conditions | | |
|---|---|---|
| Feed flow rate in g/h | 200 | 250 |
| Distillation flow rate in g/h | 122 | 175 |
| Pressure in Pa (mm Hg) | 3.7 × 10³ (50) | 1.9 × 10⁴ (140) |
| C'1 head temperature in °C. | 59 | 70 |
| C'1 compositions: | | |
| AAH (%) | 41.6 | 26 |
| EAH (%) | 41.7 | 62 |
| R'1 light ends (%) | 16.7 | 12 |
| Flow analyses | | |
| Analyses of the C'1 feed: | | |
| AA (%) | 47.2 | 47.3 |
| AA dimer (%) | 13.2 | 5.1 |
| AA trimer (%) | 1.2 | |
| EA (%) | 3.8 | 10.8 |
| EEP (%) | 4.6 | 6.3 |
| H₂O (%) | 2.2 | 2.6 |
| Hydroquinone (%) | 2.3 | |
| Analyses at the head of C'1: | | |
| AA (%) | 87.1 | 74.6 |
| EA (%) | 3.8 | 15 |
| Ethanol (%) | 1.3 | 6.3 |
| EEP (%) | 2 | <0.1 |
| H₂O (%) | 2.8 | 4 |
| Analyses at the foot of C'1: | | |
| AA (%) | 4 | 5.6 |
| AA dimer (%) | 25.7 | 18.6 |
| AA trimer (%) | 2.9 | 2.4 |
| EA (%) | <0.2 | <0.2 |
| Hydroquinone (%) | 4.8 | 3.4 |

TABLE 9

Operating conditions and results from the cracking stage.

| Operating conditions | | |
|---|---|---|
| R'1 temperature (°C.) | 218 | 218 |
| R'1 residence time (min) | 105 | 97 |
| Cracking ratio (%) | 81 | 79 |
| Flow analyses (%) | | |
| Analyses of the R'1 feed: | | |
| AA | 4 | 5.6 |
| AA dimer | 25.7 | 18.6 |
| AA trimer | 2.9 | 2.4 |
| EA | <0.2 | <0.2 |
| Hydroquinone | 4.8 | 3.4 |
| Analyses of the R'1 distillate: | | |
| AA | 54.7 | 44.6 |
| EA | 9.7 | 10.6 |
| Ethanol | 1.4 | 1.2 |
| EEP | 12.7 | 21.7 |
| $H_2O$ | 3.1 | 2.6 |

Without further elaboration, it is believed that one skilled in the art can, using the preceding description, utilize the present invention to its fullest extent.

In the foregoing examples, all temperatures are set forth uncorrected in degrees Celsius and unless otherwise indicated, all parts and percentages are by weight.

The entire disclosure of all applications, patents and publications, cited above and below, and of corresponding French application 94/14935, are hereby incorporated by reference.

We claim:

1. A process for recovery of the light noble products present in the distillation residues from processes for the manufacture of acrylic acid and of esters of the said acid and of $C_1$–$C_8$ alcohols, by thermal cracking of the said residues, the said noble products comprising acrylic acid monomer, the said acrylic ester monomers and the said alcohols, characterized in that this cracking is performed, in the absence of catalyst, on a mixture of heavy distillation residues originating, on the one hand, from the manufacture of acrylic acid and, on the other hand, from the manufacture of the abovementioned esters, in that the light fraction originating from the dissociation reactions is continuously vaporized during the cracking operation and in that this light fraction is distilled in order to recover, after condensation, the required light noble products.

2. A process according to claim 1, characterized in that the mass ratio of the heavy residues originating from the process for the manufacture of acrylic acid to the heavy residues originating from the process for the manufacture of an ester of acrylic acid is between 9/1 and 1/9.

3. A process according to claim 1, characterized in that the ester is methyl or ethyl acrylate.

4. A process according to claim 1, characterized in that the cracking is conducted at a temperature of between 140° and 260° C. with a residence time of 0.5 to 3 hours.

5. A process according to claim 1, characterized in that the distillation of the vaporized light fraction is conducted at reduced pressure.

6. A process according to claim 1, characterized in that the distillation is conducted in the presence of at least one polymerization inhibitor.

7. A process according to claim 1, characterized in that the light noble products obtained are recycled to the process for the manufacture of esters of acrylic acid from which originates the heavy resins employed jointly with the heavy residues originating from the manufacture of acrylic acid.

8. A process according to claim 1, characterized in that it is conducted continuously and comprises:

conducting the cracking of the mixture of the heavy residues to be cracked, optionally preheated, in a reactor (R1);

feeding a distillation column (C1) with the light products of the cracking;

recovering, at the head of column (C1), the required mixture of light noble products;

recycling into the reactor (R1) the flow recovered at the foot of the column (C1);

recovering the heavy residue from the reactor (R1) and sending it to a removal treatment, if appropriate after having diluted it with a part of the flow recovered at the foot of the column (C1), the remainder of the said flow being recycled into the reactor (R1).

9. A process according to claim 1, characterized in that it is conducted continuously and comprises:

sending the mixture of the heavy residues to be cracked to a distillation column (C'1);

recovering, at the head of column (C'1), a mixture of light noble products' sending the flow obtained at the foot of column (C'1) to a cracking reactor (R'1);

recycling the mixture of the light products of cracking to the distillation column (C'1);

recovering the heavy residue from the reactor (R'1) and sending it to a subsequent removal treatment, if appropriate after having diluted it with a part of the flow recovered at the foot of the column (C'1), the remainder of the said flow being sent to the cracking reactor (R'1).

* * * * *